United States Patent [19]

Tachibana et al.

[11] Patent Number: 4,942,257

[45] Date of Patent: Jul. 17, 1990

[54] METHOD OF MANUFACTURING ALKALI METAL SALT OF 2,3,6,7-NAPHTHALENETETRACARBOXYLIC ACID

[75] Inventors: Yakudo Tachibana; Kazuhiko Tate; Toshifumi Suzuki, all of Tokyo; Kouji Chiba, Miura, all of Japan

[73] Assignee: NKK Corporation, Tokyo, Japan

[21] Appl. No.: 401,635

[22] Filed: Aug. 31, 1989

[30] Foreign Application Priority Data

Sep. 5, 1988 [JP] Japan .................................. 63-221637

[51] Int. Cl.⁵ .................... C07C 51/02; C07C 51/347; C07C 51/353
[52] U.S. Cl. .................................... 562/481; 562/423; 562/482; 562/483; 562/486; 562/488
[58] Field of Search ............... 562/423, 481, 482, 483, 562/488

[56] References Cited

U.S. PATENT DOCUMENTS 4,820,868  4/1989  Mitamura et al. .................. 562/482

OTHER PUBLICATIONS

Dozen et al., Thermochim. Acta, 25, pp. 209 to 216 (1978).

Primary Examiner—Werren B. Lone
Assistant Examiner—Vera C. Clarke
Attorney, Agent, or Firm—Frishauf, Holtz, Goodman & Woodward

[57] ABSTRACT

A method of manufacturing an alkali metal salt of 2,3,6,7-naphthalenetetracarboxylic acid. Either a sodium salt or a mixture of sodium salt and potassium salt of at least one naphthalenecarboxylic acid selected form the group consisting of naphthoic acids and naphthalenepolycarboxylic acids is heated to an elevated temperature in an inert gas atmosphere in the presence of a Henkel reaction catalyst and halogenated sodium.

24 Claims, 1 Drawing Sheet

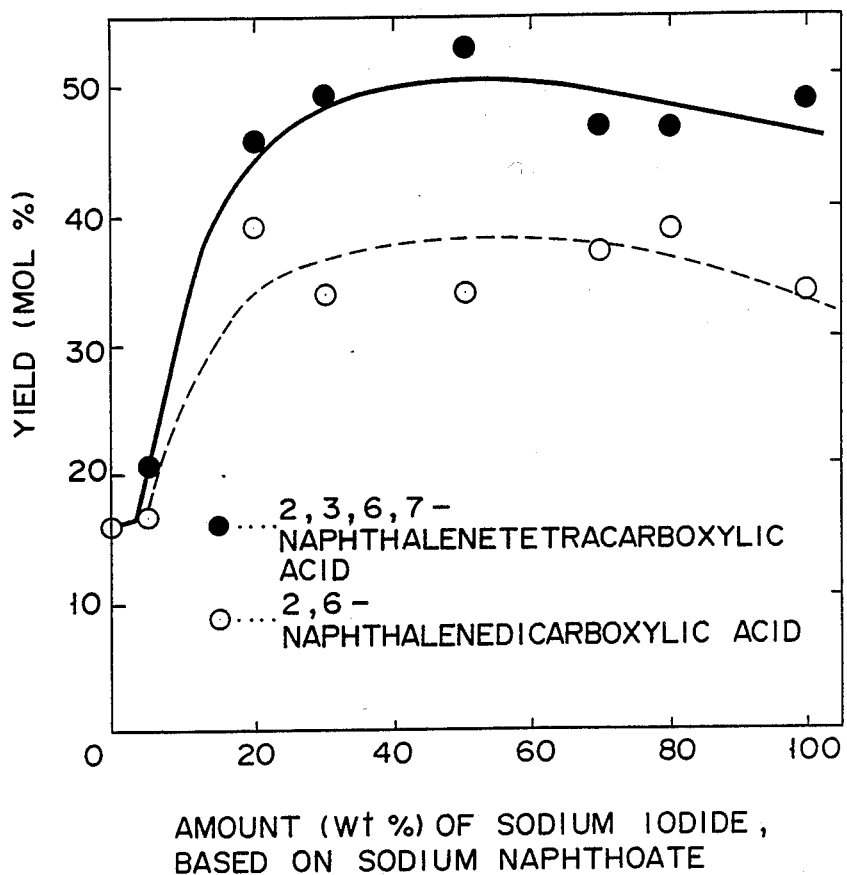
F I G. 1

4,942,257

METHOD OF MANUFACTURING ALKALI METAL SALT OF 2,3,6,7-NAPHTHALENETETRACARBOXYLIC ACID

BACKGROUND OF THE INVENTION

1. Field of the Invention

The present invention relates to a method of manufacturing an alkali metal salt of 2,3,6,7-naphthalenetetracarboxylic acid.

2. Description of the Related Art 2,3,6,7-naphthalenetetracarboxylic acid, having a symmetrical structure, like pyromellitic acid, may be useful as raw materials for various polymers and synthetic materials of plasticizing agents, dyes, or pigments.

This carboxylic acid is described in Y. Dozen, Thermochim. Acta. 25, 209–216, 1978. However, the method of preparing the acid, which is disclosed in this thesis, includes many synthesizing steps, and no methods which can be industrially satisfactory have been completed.

On the other hand, methods of manufacturing 1,3,5,7-naphthalenetetracarboxylic acid, which is one isomer of the naphthalenetetracarboxylic acids, are disclosed in several publications such as Published Unexamined Japanese Patent Application Nos. 49-102656, 49-102657, and 51-26857. Any of these methods utilizes rearrangement or disproportionation reaction of aromatic carboxyl groups, which is generally known in the art as the Henkel reaction.

The Henkel reaction is to form an aromatic dicarboxylic acid by heating an aromatic monocarboxylic acid alkali metal salt and/or a polycarboxylic acid alkali metal salt to a high temperature in an atmosphere of carbon dioxide in the presence of a catalyst such as an oxide of cadmium or zinc. This reaction has long been utilized to manufacture dipotassium terephthalate from potassium benzoate or dipotassium phthalate, and to manufacture dipotassium 2,6-naththalenedicarboxylate from potassium naphthoate or potassium naphthalate, for example. In the prior art Henkel reaction, the alkali of the alkali metal carboxylate or the alkali halide used as co-catalyst is potassium in most cases. In fact, potassium better serves to manufacture the target product at a high yield, than any other alkali. For example, when sodium salt is used in place of potassium salt, more by-product is formed, inevitably reducing the yield of the target product. In the prior patent applications relating to the Henkel reaction, though the alkali is not limited to a potassium salt in the claims of these patent applications, only a potassium salt is cased in the working examples thereof in these examples.

Published Examined Japanese Patent Application No. 36-13629 discloses a method of manufacturing terephthalate from mixed sodium and potassium phthalates, which mixed phthalates have a K/Na atomic ratio of 95/5 to 70/30. In this method, by using sodium salt in a small amount, the melting point of the mixed phthalates is lowered below that of the dipotassium phthalate, so that a lower temperature is sufficient to melt the phthalate, making it possible to produce the terephthalate at a high yield. However, the main component of the alkali is potassium in this method. The sodium salt is used to lower the melting point of the phthalate raw material and in an amount such that the yield of the terephthalate is not lowered.

A method of manufacturing pyromellitate by means of the Henkel reaction is disclosed in Published Examined Japanese Patent Application No. 45-656 in which one of the present inventors is also named as an inventor. In this method, a mixture of sodium phthalate and potassium phthalate, which has a Na/K atomic ratio of 95/5 to 70/30, is heated to a high temperature in an atmosphere of an inert gas such as carbon dioxide gas, in the presence of a Henkel reaction catalyst. This publication teaches nothing about using of a co-catalyst in the Henkel reaction.

The carboxylic acid used as the material in this method is a benzene series, whose melting point is relatively low. Therefore, the temperature to which the mixture of said salts must be heated to accomplish the Henkel reaction is comparatively low. Because of the low temperature, the carboxyl group is scarcely decomposed by heat before the material (i.e., carboxylic acid) undergoes the Henkel reaction. As a result, pyromellitic acid is produced at a high yield. Further, since the carboxylic acid used as the material, which is a benzene series, has a few positions where the carboxyl group can be substituted, the produced positional isomers are small in numbers. It is therefore relatively easy to isolate pyromellitic acid from the other reaction products, whereby pyromellitic acid can be obtained which has a high purity.

When this method is employed to process naphthalene-series carboxylate, however, it is difficult to manufacture 2,3,6,7-naphthalenetetra-carboxylic acid, for the following reason.

Most naphthalene-series compounds have a melting point higher than that of benzene-series compounds. Hence, to subject naphthalene-series carboxylate to the Henkel reaction successfully, it is necessary to heat this material to a temperature higher than a benzene-series carboxylate. Therefore, the carboxyl group is likely to be thermally decomposed before the naphthalene-series carboxylate is heated to the reaction temperature. Consequently, 2,3,6,7-naphthalenetetracarboxylic acid is obtained at a low yield. Since the carboxylic acid used as the raw material is a naphthalene series and has many positions where the carboxyl group can be substituted, the produced positional isomers are proportionally great in numbers. It is inevitably difficult to isolate 2,3,6,7-naphthalenetetracarboxylic acid from the other reaction products. Hence, the 2,3,6,7naphthalenetetracarboxylic acid, thus obtained, has but low purity.

A method other than the Henkel reaction can be used to manufacture 2,3,6,7-naphthalenetetracarboxylic acid. This method, however, includes many synthesizing steps, and can not achieve a high yield of 2,3,6,7naphthalenetetracarboxylic acid. Therefore, the method can hardly be employed on industrial scale.

SUMMARY OF THE INVENTION

Accordingly, an object of the present invention is to provide a method of manufacturing an alkali metal salt of 2,3,6,7-naphthalenetetracarboxylic acid at a high yield.

This object is attained by a method, wherein a sodium salt or a mixture of sodium salt and potassium salt of at least one naphthalenecarboxylic acid selected from the group consisting of naphthoic acids and naphthalenepolycarboxylic acids is heated to an elevated temperature in an inert-gas atmosphere in the presence of a Henkel reaction catalyst and sodium halide.

BRIEF DESCRIPTION OF THE DRAWINGS

FIG. 1 shows the relationship between the yield of 2,3,6,7-naphthalenetetracarboxylic acid and the amount (percent by weight) of sodium iodide wherein the solid curve indicates the relationship for the product according to the invention, and the broken curve indicates the relationship for a comparative example.

DETAILED DESCRIPTION OF THE PREFERRED EMBODIMENTS

The inventors hereof have been studying the Henkel reaction, in search for an efficient method of manufacturing 2,6-naphthalenedicarboxylic acid. During this study, they have found that the reaction mixture obtained by means of this reaction contains a small amount of 2,3,6,7-naphthalenetetracarboxylic acid. Then, they started researching the process of forming 2,3,6,7-naphthalenetetracarboxylic acid, and found a factor which promotes the forming of this acid. They further conducted experiments in order to invent a method which solves the aforementioned problems inherent in the prior art method and which can serve to manufacture an alkali metal salt of 2,3,6,7-naphthalenetetracarboxylic acid. The inventors have discovered that an alkali metal salt of 2,3,6,7-naphthalenetetracarboxylic acid is manufactured at a high yield when a sodium salt or a mixture of a sodium salt and potassium salt, is/are used as the material carboxylate, is subjected to the Henkel reaction in the presence of not only a Henkel reaction catalyst, but also a sodium halide used as a co-catalyst.

The carboxylic acid, i.e., the raw material, according to the invention is either a sodium salt or a mixture of sodium salt and potassium salt of at least one naphthalenecarboxylic acid selected from the group consisting of naphthoic acids and naphthalenepolycarboxylic acids.

The naphthoic acid can be either 1-naphthoic acid, 2-naphthoic acid, or a mixture of these naphthoic acids. The naphthalenepolycarboxylic acid can be naphthalenedicarboxylic acid, naphthalenetricarboxylic acid, a higher naphthalenepolycarboxylic acid, or a mixture of any two of these carboxylic acids. In any of these naphthalenepolycarboxylic acids, the carboxyl group can be substituted at any suitable position. Further, any of these naphthalenepolycarboxylic acids can be a mixture of positional isomers. However, 2,3,6,7-naphthalenetetracarboxylic acid or a substance having a high concentration of this polycarboxylic acid is not suitable as the raw material since the target product of the method according to the invention is an alkali metal salt of nothing but this polycarboxylic acid. Industrially readily available materials are: 1-naphthoic acid, 2-naphthoic acid, naphthalic acid, and the like. These acids can be used, either singly or in mixture.

The sodium salt alone can be used as the raw material carboxylic acid salt. However, an appropriate amount of potassium is preferably added to sodium salt, so that the material as a whole has a lower melting point than otherwise, and the Henkel reaction catalyst functions more actively to promote the required Henkel reaction. Preferably, the ratio of the sodium salt to the potassium salt, i.e., Na/K, is 90/10 to 70/30 (in atomic ratio). As long as the ratio, Na/K, falls within this range, the mixed carboxylic acid salts can be prepared by whichever method is applicable. For example, a powder of the sodium salt and powder of the potassium salt can be mixed by mechanical means. Alternatively, the potassium salt can be added to a solution of the sodium salt and be dissolved therein, and then the solution now containing the potassium salt is evaporated to dryness, thereby obtaining dried mixture of these alkali metal salts. Another alternative is to add the raw material carboxylic acid to the solution containing a mixture of sodium carbonate and potassium carbonate, thereby neutralizing the solution, and then to subject the neutralized solution to evaporation to dryness, thereby obtaining the mixed salts.

In other words, when the raw material used in the method according to the invention is, for example, naphthalic acid, it can be applied in the form of either a mixture of sodium naphthalate and dipotassium naphthalate or sodium-potassium naphthalate. The same holds true of the case where the raw material is any other naphthalenepolycarboxylate. The Henkel reaction catalyst and the co-catalyst are added to the mixture of salts, or to the mixed salts while the mixed salts are being prepared, thereby preparing a raw material mixture in which both the catalyst and the co-catalyst are uniformly dispersed.

The raw material mixture, thus prepared, can be subjected to the Henkel reaction in the form of particles or in any other form.

The Henkel reaction catalyst applied in this invention is a known one generally used for the Henkel reaction. In particular, a cadmium compound and a zinc compound are preferred. For example, zinc carbonate, cadmium carbonate, cadmium chloride, zinc sulfide, and cadmium oxide can be used as Henkel reaction catalysts. Of these compounds, zinc carbonate and cadmium carbonate are most desirable.

The Henkel reaction catalyst is sufficiently active by itself. Nevertheless, it can be combined with potassium and carbonic acid, thus forming a double salt which is a more active Henkel reaction catalyst (when zinc carbonate is used as the Henkel reaction catalyst, it is combined with potassium and carbonic acid, forming a zinc-potassium carbonate). When the raw material salt contains no potassium at all or a very small amount of potassium, it is difficult for the catalyst to form a double salt. Also in order to form a double salt which has a greater catalytic activity, it is desirable that the mixture of sodium salt and potassium salt have Na/K ratio ranging from 90/10 to 70/30.

In the method according to the present invention, the Henkel reaction proceeds even if no use is made of the co-catalyst. However, when sodium halide is used as a co-catalyst, the yield of the 2,3,6,7-naphthalenetetracarboxylic acid can be greatly increased. This sodium halide can include sodium chloride, sodium bromide, sodium iodide. Of these sodium halides, sodium iodide is the most preferred. The amount of the sodium halide, which should be used, depends upon the kind of the compounds. In general, the amount of sodium halide is about 5 to 100 percent by weight on the basis of the amount of the raw material salt used.

The raw material salt must be subjected to the Henkel-reaction in an atmosphere of an inert gas such as rare gas, carbon dioxide gas, nitrogen gas, or the like, which does not affect the Henkel reaction. It is particularly preferable that the reaction be carried out under pressure and in a carbon dioxide atmosphere so as to suppress the decarboxylation of carboxylate used as the material.

The reaction utilized in the present invention is apparently similar to a solid phase reaction, since the solid phase material, i.e., particles of carboxylic acid salt, is partly melted, and the molten portions of the particles undergo the reaction, thus forming a solid phase reaction product. The reaction temperature must be high enough to melt a portion of particles of carboxylic acid salt, thereby causing the Henkel reaction. It is usually 350° C. or more, preferably 400° C. to 500° C.

The reaction can be carried out either in a closed system or in a reaction system into which an inert gas is being supplied. In the method according to the invention, the raw material salt, the Henkel reaction catalyst, and the co-catalyst can be in the form of a liquid phase suspension under the above-mentioned reaction conditions. In other words, the reaction can be conducted on the raw material salt, the Henkel reaction catalyst, and the co-catalyst which are dispersed in a dispersing medium or partly dissolved in a dispersing medium. The dispersing medium can be an aprotic multiring aromatic compound having two or three aromatic rings, such as naphthalene, biphenyl or triphenyl.

The alkali metal salt of 2,3,6,7-naphthalenetetra-carboxylic acid, thus obtained, can be isolated from the following reaction product by the method below.

First, water is added to the reaction product, and the resultant solution is heated, and the solution is filtered to remove the Henkel reaction catalyst, the carbide, and the like—all insoluble in hot water. A mineral acid is added to the filtrate, thereby adjusting the acidity of the filtrate to pH 3 and precipitating the unreacted substances such as dicarboxylic acid. These substances are filtered out, thus preparing a filtrate containing acidic water-soluble carboxylic acids. An alkali is added to this filtrate, adjusting the acidity thereof to pH 8. Further, calcium chloride is added to the acidity-adjusted solution, and the solution is heated, thus causing a double decomposition reaction on this solution. As a result of the decomposition, the 2,3,6,7-naphthalenetetracarboxylate is insolubilized as a calcium salt, which precipitates. This precipitate is filtered out from the solution. Then, the water-soluble substance is acid-decomposed at the acidity of pH 1 or less, thereby obtaining 2,3,6,7-naphthalenetetracarboxylic, acid and/or an anhydride thereof.

When the reaction has been carried on the liquid-phase suspension in the above-noted dispersing medium, an appropriate organic solvent (e.g., benzene, naphthalene, or the like) is added, if necessary, to the liquid phase reaction product, thus adjusting the viscosity thereof. Thereafter, hot water is added to the suspension, separating the substance insoluble in hot water and the water layer containing the target product, from each other. The water layer, thus obtained, can be treated in the method described above to obtain the desired carboxylic acid and/or an anhydride thereof.

The product made by means of the Henkel reaction is mainly 2,6-naphthalenedicarboxylic acid, except for 2,3,6,7-naphthalenetetracarboxylic acid. The 2,6-naphthalenedicarboxylic acid can be separated from the 2,3,6,7-naphthalenetetracarboxylic acid and refined according a conventional method. The refined 2,6naphthalenedicarboxylic acid can be used for other applications. Alternatively, after recovery of 2,3,6,7-naphthalenetetracarboxylic acid, the crude 2,6-naphthalenedicarboxylic acid containing other naphthalenecarboxylic acids can be used as the raw material carboxylic acid to be subjected to the Henkel reaction.

As has been pointed out, the Henkel reaction catalyst is insoluble in hot water and is contained, along with the carbide, in the substance filtered out of the hot aqueous solution. Hence, the catalyst can readily be collected from the filtrate and regenerated by means of the conventional method, and can be repeatedly utilized in the Henkel reaction.

The sodium halide, which is used as co-catalyst in the Henkel reaction, can be collected for re-use, in the following method. First, the 2,3,6,7-naphthalenetetracarboxylic acid is precipitated as a calcium salt in the way specified above. This acid, in the form of a precipitate, is filtered from the solution. Carbon dioxide gas is blown into the solution, combining with the residual calcium in the solution, thus forming calcium carbonate in the form of a precipitate. This precipitate is filtered out. The resultant filtrate was evaporated to dryness, whereby the sodium halide, containing an alkali salt of the mineral acid, is collected. Needless to say, the sodium halide thus collected can be used again as a co-catalyst.

The solution, from which the residual calcium has been filtered out, can be utilized as the solvent for the preparation of the mixed salts of the raw material carboxylic acids. The solution is useful since it contains the co-catalyst.

Furthermore, when an alkali is used in the above separating method has an Na/K ratio ranging from 90/10 to 70/30, the solution also has an Na/K ratio falling within this range. The unreacted substances, such as dicarboxylic acid, which have been precipitated by adding the mineral acid to the filtrate, thereby adjusting the acidity of the filtrate, is mixed with the solution, thereby obtaining material carboxylate having an Na/K ratio ranging from 90/10 to 70/30. This carboxylate is a very useful starting material.

In the separation method described above, the alkali metal salt of the mineral acid returns to the reaction system, along with the co-catalyst (i.e., sodium halide). Nevertheless, the alkali metal salt of the mineral acid cause no problems if is present in the next Henkel reaction since it does not hinder the Henkel reaction at all. Particularly, a hydrogen halide acid is a preferable mineral acid since it forms an alkali metal salt which can function as a co-catalyst.

According to the present invention, as has been stated, either a sodium salt or a mixture of sodium salt and potassium salt of naphthoic acids and/or naphthalenecarboxylic acids, is used as a material salt, whose melting point is low. Further, since the main alkali source and the co-catalyst, used in the invention, are sodium and sodium halide, respectively, the Henkel reaction temperature can be lowered. This effectively facilitates the disproportionation reaction of the naphthalene carboxylic acid. As a result, naphthalenetetracarboxylic acid can be manufactured at a high yield.

EXAMPLE 1

First, 20.8 g of disodium naphthalate, 5.8 g of dipotassium naphthalate, 20.0 g of sodium iodide, and 3.0 g of cadmium oxide were crushed and mixed together in a mortar, until they formed a homogeneous mixture. This mixture was dried thoroughly at 150° C. The dried mixture was placed in a 100 ml-autoclave made of stainless steel. After the autoclave was fully purged with carbon dioxide gas, carbon dioxide gas was introduced thereinto until the internal pressure of the autoclave reached 30 kg/cm$^2$ G. Then, the autoclave was heated in an electric furnace at 460° C. for three hours. Thereafter, the autoclave was cooled to room temperature, and its pressure was released. The contents were dissolved in 300 ml of water by heating the water. The insolubles were filtered out of the aqueous solution by suction. A proper amount of 6N-hydrochloric acid solution was added to the resultant filtrate, thereby adjusting the acidity thereof to pH 3. The precipitate was filtered out. An appropriate amount of 6N-sodium hydroxide aqueous solution was added to the resultant filtrate, thus adjusting the acidity thereof to pH 8. Further, 25 g of calcium chloride (hexahydrate) was added to the filtrate. The filtrate was heated for 30 minutes, while being stirred, thereby precipitating the dicalcium salt of 2,3,6,7-naphthalenetetracarboxylic acid. This precipitate was filtered out, and dried at 150° C.

The amount of the dicalcium salt of 2,3,6,7-naphthalenetetracarboxylic acid, thus obtained, was 11.8 g, which corresponds to a yield of 62.2% on the basis of the carboxyl group of the material naphthalic acid.

EXAMPLE 2

First, 15.5 g of 1-sodium naphthoate, 4.2 g of 2-potassium naphthoate, 20.0 g of sodium iodide, and 3.0 g of cadmium oxide were crashed and mixed together in a mortar, till they formed a homogeneous mixture. This mixture was dried, and then subjected to the same reaction as in Example 1, thereby obtaining dicalcium salt of 2,3,6,7-naphthalenetetracarboxylic acid.

The amount of the dicalcium salt thus obtained was 6.2 g, which corresponds to a yield of 65.3% on the basis of the carboxyl group of the material naphthalic acid.

EXAMPLE 3

First, 1.40 g of sodium 1-naphthoate, 0.70 g of sodium iodide, and 0.07 g of cadmium oxide were crashed and mixed together in a mortar, until they form a homogeneous mixture. The mixture was thoroughly dried at 150° C. The mixture, thus dried, was placed within an autoclave made of stainless steel. After the autoclave was fully purged with carbon dioxide gas, carbon dioxide gas was introduced thereinto until the internal pressure of the autoclave reached 30 kg/cm$^2$G. The autoclave was heated in an electric furnace at 480° C. for one hour. Thereafter, the autoclave was cooled to room temperature, and its pressure was released. The contents were dissolved in 30 mg of water by heating the water in a flask equipped with a reflux condenser. The insolubles including cadmium oxide, naphthalene, and carbide, were filtered out from the aqueous solution. An excessive amount (3.0 g) of silver nitrate was dissolved in a small amount of water, thus forming an aqueous solution. This solution was added to the filtrate, thus preparing a suspension. This suspension was heated in a hot bath for one hour. The suspension was then cooled, allowing a silver salt of naphthalenecarboxylic acids and also silver iodide to precipitate. These precipitates were filtered out, and dried in a vacuum. The dried precipitates were crushed into powder. The powder was suspended in a solution consisting of 100 ml of benzene and 2 ml of methyl iodide, thus forming a suspension. This suspension was heated in a hot bath for eight hours, and then cooled, allowing the silver iodide to precipitate. The precipitated silver iodide was filtered from the suspension, leaving in the filtrate a methyl ester solution of naghthalenecarboxylic acids.

This methyl ester solution was analyzed by means of a gas chromatograph having a capillary column manufactured by Simazu Co., Ltd. (HiCap CBP 10-M50-025), heated at a column temperature of 220 to 300° C. with a column heating rate of 10° C./min, and supplied with carrier gas (nitrogen gas) at a rate of 0.3 ml/min, thereby measuring the yields of the naphthalenecarboxylic acids produced by the Henkel reaction. The results were as is shown in Table 1, wherein the yields represented are based on the carboxyl group of the material naphthoic acids.

TABLE 1

| Reaction Product | Yield (mol %) |
|---|---|
| 2,3,6,7-naphthalenetetracarboxylic acid | 53.2 |
| 2,6-naphthalenedicarboxylic acid | 34.6 |
| 2,3,6-naphthalenetricarboxylic acid | 5.0 |
| 2,3-naphthalenedicarboxylic acid | 2.2 |
| 2-naphthoic acid | 1.7 |
| Total | 96.7 |

EXAMPLE 4

A proper amount of sodium naphthoate used as material, and 0 to 100 percent by weight of sodium iodide used as co-catalyst, on the basis of the sodium naphthoate, were crushed and mixed together in a mortar, until they formed a homogeneous mixture. The mixture was then processed in the same way as in Example 3, and the same steps as carried out in Example 3 were performed, thereby preparing various reaction products. The yields of the main product of 2,3,6,7-naphthalenetetracarboxylic acid and the by-product of 2,6-naphthalenedicarboxylic acid, were measured in mol percent based on the carboxyl group of the naphthoic acid. The yields of these products, and the content of the sodium iodide had the relationship illustrated in FIG. 1.

COMPARATIVE EXAMPLE

The same procedures were followed as in Example 1, except that the co-catalyst, sodium iodide, was not used.

The amount of the 2,3,6,7-naphthalenetetracarboxylic acid thus obtained was 3.5 g, which corresponds to a yield of 18.4% on the basis of the carboxyl group of the raw material naphthalic acid.

What is claimed is:

1. A method of manufacturing an alkali metal salt of a 2,3,6,7-naphthalenetetracarboxylic acid, comprising heating (i) a sodium salt or (ii) a mixture of sodium salt and potassium salt, of at least one naphthalenecarboxylic acid selected from the group consisting of naphthoic acids and naphthalenepolycarboxylic acids other than 2,3,6,7-naphthalenetetracarboxylic acid to an elevated temperature in an inert gas atmosphere in the presence of a Henkel reaction catalyst and sodium halide to convert said salt or mixture of salts of said at least one naphthalenecarboxylic acid into said 2,3,6,7-naphthalenetetracarboxylic acid salt or salts.

2. The method according to claim 1, wherein said mixture of sodium salt and potassium salt has an Na/K atomic ratio of from 90/10 to 70/30.

3. The method according to claim 1, wherein said sodium salt is a sodium halide is used in an amount of from 5 to 100 percent by weight on the basis of said sodium salt or mixture of said sodium salt and potassium salts of said at least one naphthalenecarboxylic acid.

4. The method according to claim 1, wherein said sodium halide is sodium iodide.

5. The method according to claim 1, wherein said naphthalenepolycarboxylic acid is selected from the group consisting of naphthalenedicarboxylic acid isomers, naphthalenetricarboxylic acid isomers, and a mixture thereof.

6. The method according to claim 1, wherein said Henkel reaction catalyst is selected from the group consisting of cadmium oxides and zinc oxides.

7. The method according to claim 1, wherein said heating is at a temperature sufficient to partially melt said sodium salt or mixture of said sodium and potassium salts of said at least one naphthalenecarboxylic acid.

8. The method according to claim 1, wherein said heating is effected at a temperature of 350° C. or more.

9. The method according to claim 1, wherein said inert-gas atmosphere comprises carbon dioxide gas.

10. The method according to claim 5, wherein said sodium halide is in an amount of from 5 to 100% by weight on the basis of the total of said sodium salt or mixture of sodium and potassium salts of said at least one naphthalenecarboxylic acid; and wherein said heating is at a temperature sufficient to partially melt said sodium salt or mixture of said sodium and potassium salts of said at least one naphthalenecarboxylic acid.

11. The method according to claim 10, wherein a mixture of sodium and potassium salts of said at least one naphthalenecarboxylic acid is used; said mixture has a Na/K ratio of from 90/10 to 70/30; and wherein said sodium halide is selected from the group consisting of iodide, bromide and chloride.

12. The method according to claim 10, wherein the sodium iodide is used; and said salt of said at least one naphthalenecarboxylic acid is the sodium salt which is heated to a temperature of at least 350° C. in an inert atmosphere comprising carbon dioxide gas.

13. The method according to claim 11, wherein the sodium iodide is used; and said salt of said at least one naphthalenecarboxylic acid is the mixture of the sodium and potassium salts which is heated to a temperature of at least 350° C. in an inert atmosphere comprising carbon dioxide gas.

14. The method according to claim 12, wherein said Henkel reaction catalyst is selected from the group consisting of cadmium oxides and zinc oxides.

15. The method according to claim 13, wherein said Henkel reaction catalyst is selected from the group consisting of cadmium oxides and zinc oxides.

16. The method according to claim 1, wherein said at least one naphthalenecarboxylic acid comprises at least one selected from the group consisting of 1-naphthoic acid, 2-naphthoic acid and 2,6-naphthalenedicarboxylic acid.

17. The method according to claim 14, wherein said at least one naphthalenecarboxylic acid comprises at least one selected from the group consisting of 1-naphthoic acid, 2-naphthoic acid and 2,6-naphthalenedicarboxylic acid.

18. The method according to claim 15, wherein said at least one naphthalenecarboxylic acid comprises at least one selected from the group consisting of 1-naphthoic acid, 2-naphthoic acid and 2,6-naphthalenedicarboxylic acid.

19. The method according to claim 13, wherein said at least one naphthalenecarboxylic acid is at least one selected from the group consisting of 1-naphthoic acid, 2-naphthoic acid, and wherein said method produces the salt of 2,6-naphthalenedicarboxylic acid in addition to producing said salt of said 2,3,6,7-naphthalenetetracarboxylic acid.

20. The method according to claim 14, wherein said at least one naphthalenecarboxylic acid is at least one selected from the group consisting of 1-naphthoic acid, 2-naphthoic acid, and wherein said method produces the said salt of 2,6-naphthalenedicarboxylic acid in addition to producing said salt of said 2,3,6,7-naphthalenetetracarboxylic acid.

21. The method according to claim 15, wherein said at least one naphthalenecarboxylic acid is at least one selected from the group consisting of 1-naphthoic acid, 2-naphthoic acid, and wherein said method produces the said salt of 2,6-naphthalenedicarboxylic acid in addition to producing also salt of said 2,3,6,7-naphthalenetetracarboxylic acid.

22. The method according to claim 19, wherein said salt of 2,6-naphthalenedicarboxylic acid product of said method is recycled and utilized as at least part of said salt or salts of said at least one naphthalenecarboxylic acid in the heating step of said process.

23. The method according to claim 20, wherein said salt of 2,6-naphthalenedicarboxylic acid product of said method is recycled and utilized as at least part of said salt or salts of said at least one naphthalenecarboxylic acid in the heating step of said process.

24. The method according to claim 21, wherein said salt of 2,6-naphthalenedicarboxylic acid product of said method is recycled and utilized as at least part of said salt or salts of said at least one naphthalenecarboxylic acid in the heating step of said process.

* * * * *